US009489494B2

(12) United States Patent
Ripp et al.

(10) Patent No.: US 9,489,494 B2
(45) Date of Patent: Nov. 8, 2016

(54) RECOMMENDATION ENGINE

(71) Applicant: Dunlop Sports Company Limited, Kobe (JP)

(72) Inventors: Patrick A. Ripp, Seal Beach, CA (US); Michael J. Kline, Huntington Beach, CA (US)

(73) Assignee: Dunlop Sports Company Limited, Kobe (JP)

( * ) Notice: Subject to any disclaimer, the term of this patent is extended or adjusted under 35 U.S.C. 154(b) by 218 days.

(21) Appl. No.: 14/310,982

(22) Filed: Jun. 20, 2014

(65) Prior Publication Data

US 2015/0367222 A1     Dec. 24, 2015

(51) Int. Cl.
*G06F 19/00*     (2011.01)
*G06Q 30/06*     (2012.01)

(52) U.S. Cl.
CPC ....... *G06F 19/3481* (2013.01); *G06Q 30/0621* (2013.01)

(58) Field of Classification Search
USPC .................................................. 473/407, 409
See application file for complete search history.

(56) References Cited

U.S. PATENT DOCUMENTS

| 5,558,334 | A * | 9/1996 | Roche ................ A63B 69/3652 473/279 |
| 6,224,493 | B1 | 5/2001 | Lee et al. |
| 6,592,473 | B2 | 7/2003 | McDonald et al. |
| 7,121,962 | B2 | 10/2006 | Reeves |
| 7,967,695 | B2 | 6/2011 | Voges et al. |
| 8,210,960 | B1 | 7/2012 | Davenport |
| 8,221,257 | B2 | 7/2012 | Davenport |
| 8,267,812 | B1 | 9/2012 | Sery |
| 8,337,335 | B2 | 12/2012 | Dugan |
| 8,360,899 | B2 | 1/2013 | Swartz et al. |
| 8,371,962 | B2 | 2/2013 | Solheim et al. |
| 8,414,411 | B2 | 4/2013 | Stites et al. |
| 8,430,770 | B2 | 4/2013 | Dugan |
| 8,444,509 | B2 | 5/2013 | Swartz et al. |
| 8,647,215 | B2 * | 2/2014 | Falls ...................... A63B 57/00 473/218 |
| 2005/0032582 | A1 | 2/2005 | Mahajan et al. |
| 2005/0227791 | A1 | 10/2005 | McCreary et al. |
| 2007/0049393 | A1 | 3/2007 | Gobush |
| 2007/0129178 | A1 | 6/2007 | Reeves |
| 2009/0088276 | A1 | 4/2009 | Solheim et al. |
| 2012/0077626 | A1 * | 3/2012 | Falls ...................... A63B 57/00 473/407 |
| 2012/0179418 | A1 | 7/2012 | Takasugi et al. |
| 2012/0277015 | A1 | 11/2012 | Boyd et al. |
| 2012/0289354 | A1 | 11/2012 | Cottam et al. |
| 2013/0158928 | A1 | 6/2013 | Hogdal |
| 2013/0267335 | A1 | 10/2013 | Boyd et al. |
| 2013/0267336 | A1 | 10/2013 | Boyd et al. |
| 2013/0267337 | A1 | 10/2013 | Boyd et al. |
| 2013/0267338 | A1 | 10/2013 | Boyd et al. |
| 2013/0267339 | A1 | 10/2013 | Boyd et al. |
| 2015/0065264 | A1 * | 3/2015 | Beck ...................... A63B 53/00 473/335 |
| 2016/0096088 | A1 * | 4/2016 | Beck ...................... A63B 53/00 473/282 |

\* cited by examiner

*Primary Examiner* — Pierre E Elisca

(74) *Attorney, Agent, or Firm* — Stetina Brunda Garred & Brucker

(57) ABSTRACT

Generally, described are methods, apparatuses and systems for a recommendation engine which determines a recommendation based upon a terrestrial parameter and an overall factor unrelated to the terrestrial parameter. The recommendation engine may receive as inputs: (1) some data relating to the terrestrial parameter and (2) some data relating to user operation of a mechanical device. An overall factor may be calculated or obtained, at least in part, from the data relating to user operation of the mechanical device. And based upon the data relating to the terrestrial parameter and the overall factor, a recommendation may be determined and transmitted. In one embodiment, as part of the transmission process, the recommendation may be displayed to a user requesting the recommendation.

20 Claims, 8 Drawing Sheets

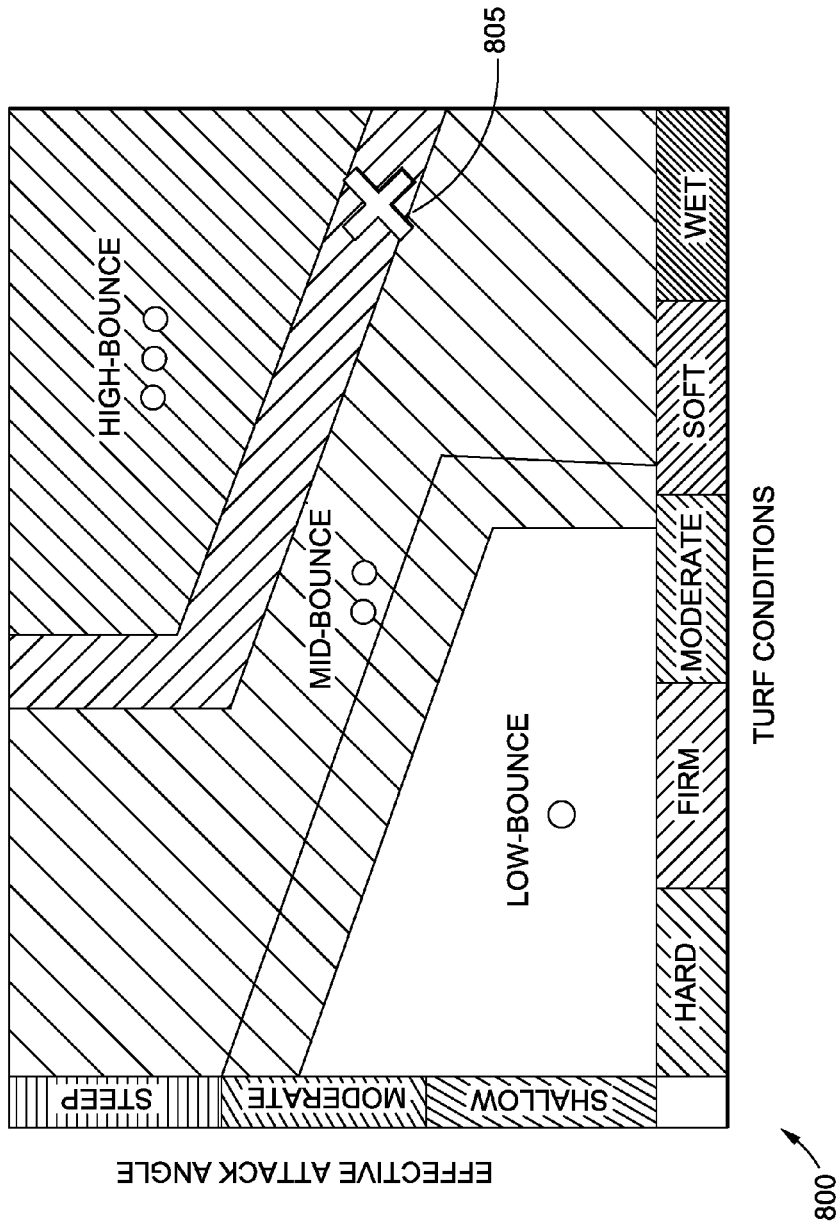

RECOMMENDATION ENGINE

COPYRIGHT AUTHORIZATION

The disclosure below may be subject to copyright protection. The copyright owner has no objection to the facsimile reproduction by any one of the documents containing this disclosure as they appear in the Patent and Trademark Office records, but otherwise reserves all applicable copyrights.

BACKGROUND

We live in a world today where customizing consumer products to the individual or individualizing devices to better fit the task at hand is becoming more and more commercially viable as technology continues to improve at a rapid rate. Rather than a "one size fits all" approach, society has continued to shift toward "finding the best fit" for the individual. For example, in the golf equipment industry, manufacturers currently offer their customers various fitting applications to improve their equipment selection. By tailoring the equipment to the individual golfer's swing type, skill level, and the like, the individual golfer knows that he or she is being given the best chance to succeed on the course.

Available customization techniques are, however, still limited in that they assume too much, namely that all golfers play on the same "average" course with "average" terrain, when in reality, each golf course is different, and terrain conditions (e.g., turf conditions) upon which the golf course sits differs from one location to another. For example, golf courses in the southeastern United States may receive more rain, and thus result in a wetter, softer environment than golf courses in the western United States, which typically has a drier and firmer environment. All other things being equal, an average golfer who primarily plays golf in Florida might be better equipped with one set of clubs suited for the environmental conditions common to Florida, while the same average golfer who primarily plays golf in California might be better equipped with another set of clubs suited for the environmental conditions common to California. Therefore, a golf-fitting professional might be able to provide more accurate recommendations for golf clubs to an individual golfer if the professional can account for the environmental conditions in which the individual golfer is likely to primarily use the clubs.

What is needed is a system that provides recommendations based upon the specific environment on which the device is primarily to be used.

SUMMARY

This summary is included to introduce, in an abbreviated form, various topics to be elaborated upon in the Detailed Description. The objects, features and advantages described herein are not intended to be limiting and will become more apparent from the following detailed description, which proceeds with reference to the accompanying figures.

Generally, one or more embodiments relate to a system for determining a recommendation based upon a terrestrial parameter and an overall factor unrelated to the terrestrial parameter. The system may receive as inputs: (1) some data relating to the terrestrial parameter; and (2) some data relating to user operation of a mechanical device. The overall factor may be calculated or obtained, at least in part, from the data relating to user operation of the mechanical device. And based upon the data relating to the terrestrial parameter and overall factor, a recommendation may be determined and transmitted. In one embodiment, as part of the transmission process, the recommendation may be displayed to a user requesting the recommendation.

In one embodiment, a non-transitory computer readable storage medium stores instructions that when executed by a processor performs the steps of: (1) receiving input corresponding to a terrestrial parameter (e.g., a turf condition of a geographical area selected from one of: hard, firm, moderate, damp, or wet); (2) receiving data characteristics of a user operating a mechanical or electro-mechanical device (e.g., a sensor detecting and obtaining data from a golfer swinging a golf club, where the sensor may be attached to the club, the golfer or attached to neither the club or golfer); (3) determining an overall factor based on the data (e.g., using attack angle data and shaft lean data obtained from the golfer's swing and calculating an effective attack angle); (4) determining a recommendation based on the overall factor and terrestrial parameter (e.g., based on the effective attack angle and the selected turf condition, using a look-up table or database to recommend a wedge-type golf club with the appropriate bounce); and (5) transmitting the determined recommendation (e.g., displaying the recommendation on a mobile electronic device).

In another embodiment, a method for obtaining a bounce recommendation may include the steps of: (1) receiving a selected geographical factor such as turf condition; (2) receiving characteristic data corresponding to a golf swing; (3) determining, using a factor determination module, an effective attack angle based on the characteristic golf swing data; (4) selecting, using a selection module, a bounce recommendation based on the effective attack angle and the geographical factor; and (5) displaying, on a graphical user interface, the selected bounce recommendation.

In another embodiment, a system for determining and displaying a bounce recommendation for a wedge-type golf club may include: (1) a swing sensing device configured to obtain data corresponding to a characteristic of a golf swing, the swing sensing device further including: (A) a sensor configured to obtain the data corresponding to the characteristic of the golf swing, and (B) a transceiver configured to send the obtained data corresponding to the characteristic of the golf swing. The system may further include: (2) a display device configured to determine and display a bounce recommendation based at least in part on the data corresponding to the characteristic of the golf swing, the display device further including: (A) an input device configured to obtain a user selected geographical factor, (B) a transceiver configured to receive the obtained data corresponding to the characteristic of the golf swing from the swing sensing device, (C) a factor determination module configured to determine an effective attack angle based on the data received from the sensor, (D) a memory device configured to store information defining a recommendation set, the recommendation set correlated to effective attack angles and geographical factors, (E) a selector configured to determine a bounce recommendation from the recommendation set based on the determined effective attack angle and the user selected geographical factor, and (F) a display configured to display the bounce recommendation.

For the golf-fitting professional, one or more embodiments may be used as a tool to further explain and/or justify recommendations for bounce, as related to customizing selection of a wedge-type golf club. In some instances, the golf-fitting professional may utilize the tool as a part of a wedge fitting. Alternatively, the tool may be used to recommend a bounce option to assist a golfer with their wedge selection.

BRIEF DESCRIPTION OF THE DRAWINGS

The features, objectives, and advantages of the present application will become more apparent from the detailed description set forth below when taken into conjunction with the drawings, wherein:

FIG. 8 illustrates a bounce recommendation display in accordance with one or more embodiments.

DETAILED DESCRIPTION

Figure 1:
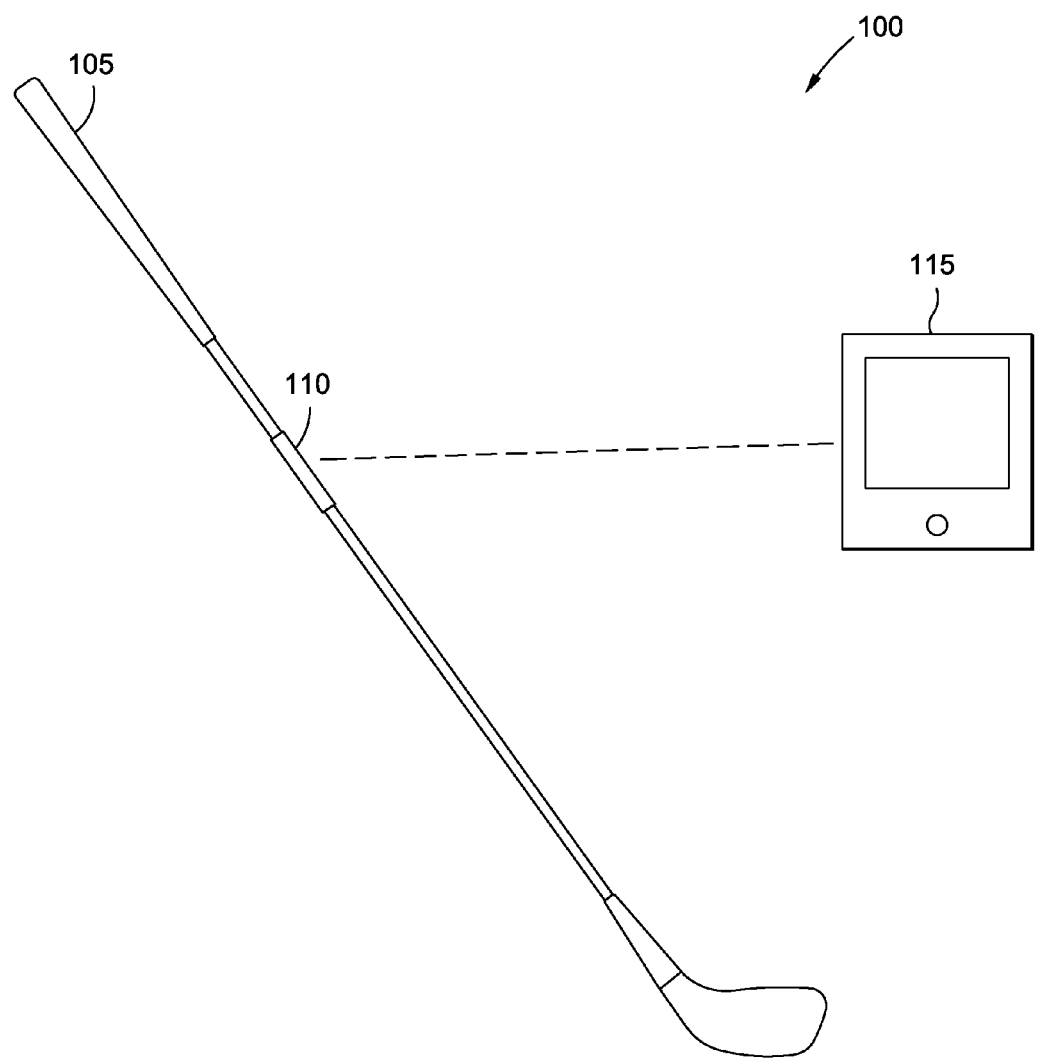
FIG. 1 is a system for determining a recommendation in accordance with one or more embodiments.

Apparatuses, systems and/or methods that implement the embodiments of the various features of the disclosure will now be described in reference to the drawings. The drawings and associated descriptions are provided to illustrate certain embodiments and are not to limit the scope of the claims. It is to be understood that other embodiments may be utilized and structural and functional modifications may be made. Throughout the drawings, references are re-used to indicate correspondence between the referenced elements.

Generally, the concepts described herein relate to a golf club (e.g., a driver, fairway, iron, wedge, putter, etc.). These concepts, however, can be applied to other devices in the sports industry that are played on various different terrains (e.g., a hockey stick that might be used on cement-paved streets in street hockey, on grass or dirt in field hockey, or on ice for ice hockey) or even devices outside the sports industry where turf condition may be a factor (e.g., lawn care, construction, etc.). For the sake of clarity and brevity, the concepts will be described in detail below with respect to a wedge-type golf club.

For clarity, "computer-readable medium" as used herein includes not only a single physical medium or single type of medium, but also a combination of one or more physical media and/or types of media. Examples of a non-transitory computer-readable medium include, but are not limited to, one or more memory chips, hard drives, optical discs (such as CDs or DVDs), magnetic discs, and magnetic tape drives. A computer-readable medium may be considered part of a larger device or it may be itself removable from the device. For example, a commonly-used removable computer-readable medium is a universal serial bus (USB) memory stick that interfaces with a USB port of a device.

In some embodiments, the disclosure may be described in the general context of computer-executable instructions, such as program modules, being executed by a computer. Generally, program modules include routines, programs, objects, components, data structures, etc. that perform particular tasks or implement particular conceptual data types. The disclosure may also be practiced in distributed computing environments where tasks are performed by remote processing devices that are linked through a communications network. In a distributed computing environment, program modules may be located in both local and remote computer storage media including memory storage devices.

In some embodiments, the disclosure is operational with numerous other general purpose or special purpose computing environments or configurations. For example, in a sales environment, the disclosure may be operational with other hand-held or laptop devices, point of sale devices, computers having access or storing inventory databases to provide a complete fitting and purchase experience to the consumer.

"Bounce angle" (sometimes "bounce") as used herein may be understood to refer to the angle formed between the leading and trailing edges of the golf club head in relationship to the ground plane when the golf club head is substantially squared and where the hosel plane is substantially perpendicular to the ground.

"Shaft lean" as used herein is measured at impact and is the angle between the shaft axis and the plane normal to the ground.

"Attack angle" as used herein is defined as an angle at which the golf club head travels with respect to the ground plane.

With respect to shaft lean and attack angle, many devices are well known for measuring such golf swing parameters with respect to golf club swings. For example, Swingbyte, headquartered in Chicago, Ill. provides a mobile golf swing analysis device attachable to a golf club shaft which measures swing characteristics and transmits the information to a paired smartphone or tablet. TrackMan, headquartered in Denmark, provides a simulator which uses high speed cameras and computing software to measure swing characteristics. In addition to these examples, other systems for determining golf swing parameters are available and well known in the field of golf.

Turning to FIG. 1, a system 100 for determining a wedge-type golf club recommendation may include a golf club 105 having mounted thereon a swing sensing device 110 in wireless communication with a mobile communication device 115. The swing sensing device 110 may be configured to obtain swing characteristics when a golfer or robot arm swings the golf club 105. For example, the sensor 110 may detect a swing path of the golf club, swing speed, etc. Beyond a mounted sensor, other data collecting methods are well known in the art and include sensors attachable to the golfer's hand or arm, glove, apparel, video analysis, etc.

Once the desired swing characteristic data is obtained from the swing, the data may be transmitted to the mobile communication device 115 via any of a number of well-known data transmitting standards (e.g., BLUETOOTH).

Figure 2:
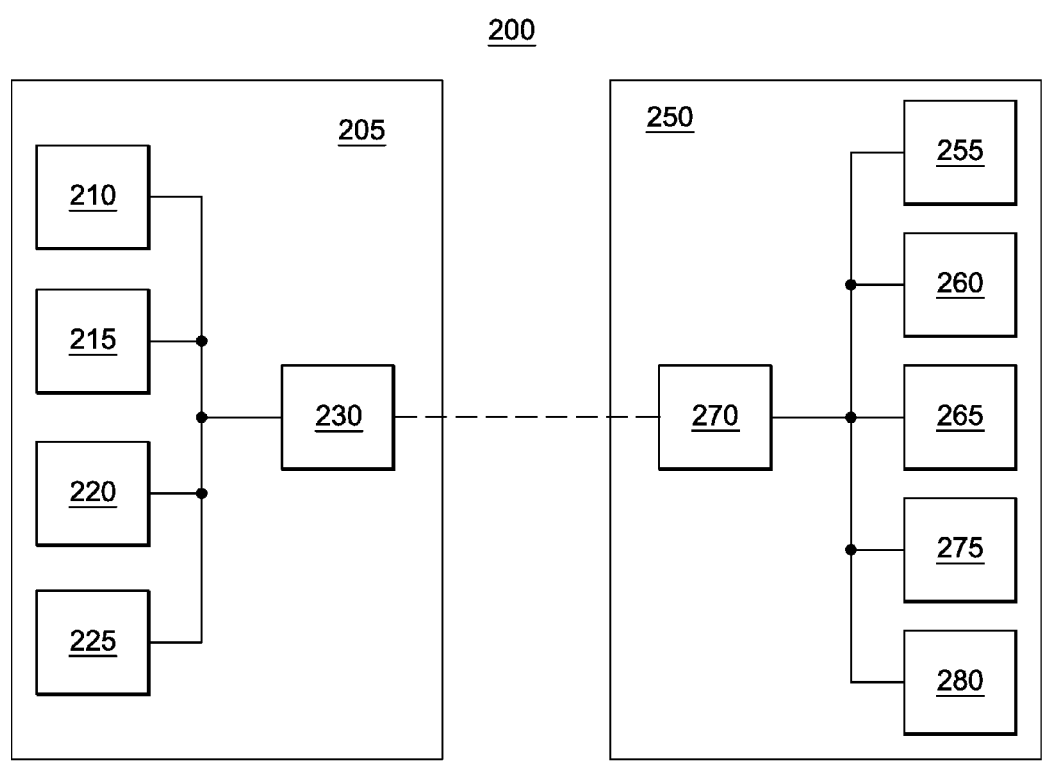
FIG. 2 illustrates a block diagram of a system for determining a recommendation in accordance with one or more embodiments.

FIG. 2 illustrates a block diagram of a system 200 for determining a recommendation in accordance with one or more embodiments. As shown, a data-obtaining device 205 (e.g., the swing sensing device 110 of FIG. 1) may be configured to allow for two-way electronic communication with a computing device 250 (e.g., the mobile communication device 115 of FIG. 1). The data-obtaining device 205 may, in one or more embodiments, be considered a special purpose computer and may further include a processor 210 for controlling overall operation of the device 205 and its associated components, including memory 215, sensor 220, Input/Output (I/O) 225, and transceiver 230. The sensor 220 may include an accelerometer and/or other devices for tracking movement, speed, position, etc.

The computing device 250 may, in one or more embodiments, be considered a special purpose computer and may further include a processor 255 for controlling operation of the device 250 and its associated components including memory 260, I/O 265, transceiver 270, selector module 275 and factor determination module 280. In one or more embodiments, the functions of selector module 275 and factor determination module 280 may be performed by processor 255.

I/O 225 and I/O 265 may each include a microphone, keypad, touch screen, camera, and/or stylus through which a user of device 205 and device 250, respectively, may provide input, and may also include one or more of a speaker for providing audio output and a video display device for providing textual, audiovisual and/or graphical output. Other I/O devices through which a user and/or other device may provide input to device 205 and/or device 250 also may be included. Software may be stored within memory 215 and/or storage to provide instructions to processor 210 for enabling data obtaining device 205 to perform various functions. For example, memory 215 may store software used by the processor 210, such as an operating system and/or application programs. Alternatively, some or all of the computer executable instructions may be embodied in hardware or firmware (not shown).

Similarly, software may be stored within memory 260 and/or storage to provide instructions to processor 255 for enabling computing device 250 to perform various functions. For example, memory 260 may store software used by the processor 255, such as an operating system and/or application programs. Alternatively, some or all of the computer executable instructions may be embodied in hardware or firmware (not shown).

In one or more embodiments, the software discussed herein may be generally understood to be stored on a computer-readable medium in the form of computer-readable instructions. A computer may read those computer-readable instructions, and in response perform various steps as defined by those computer-readable instructions. Thus, any functions attributed to any of the functional blocks of FIG. 2 as described herein may be implemented, for example, by reading and executing such computer-readable instructions for performing those functions, and/or by any hardware subsystem (e.g., a processor) from which the computer is composed.

A computer-readable medium may store computer-readable instructions (e.g., software) and/or computer-readable data (i.e., information that may or may not be executable). In the present example, a computer-readable medium (such as memory) may be included in any one or more of the functional blocks shown in FIG. 2 and may store computer-executable instructions and/or data used by any of those functional blocks. Alternatively or additionally, such a computer-readable medium storing the data and/or software may be physically separate from, yet accessible by, any of the functional blocks shown in FIG. 2.

Although various components are illustrated in one or more of the figures, it should be understood that any combination of the various components may be utilized in different embodiments. Any combination of components is within the scope of the disclosure. For example, instead of having two separate devices comprising the system 200, an artisan may combine the functionality into one comprehensive device.

Figure 3:
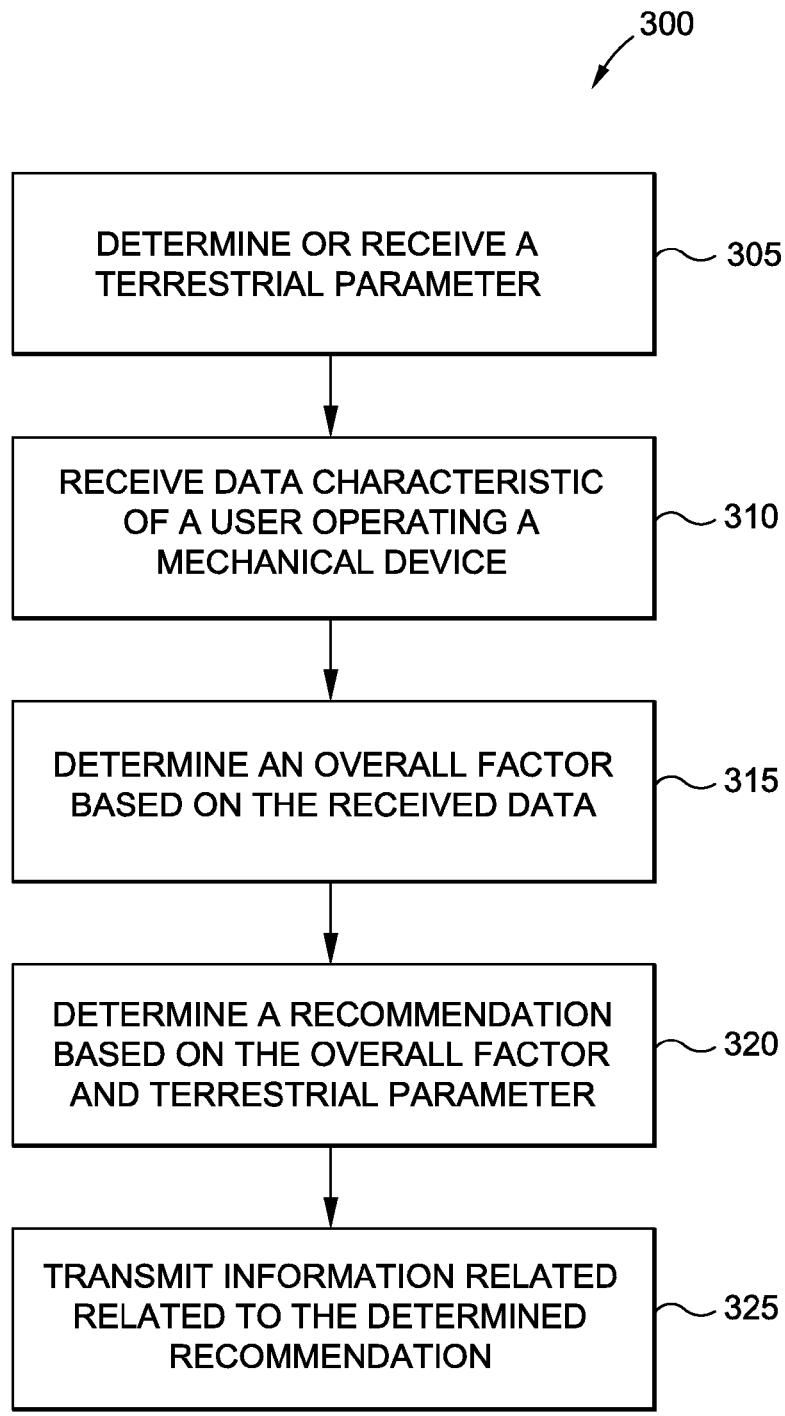
FIG. 3 illustrates a flow chart for determining a recommendation based on an overall factor and a terrestrial parameter in accordance with one or more embodiments.

FIG. 3 illustrates a flow chart 300 for a recommendation based upon a terrestrial parameter and an overall factor (e.g., as executed by system 100 of FIG. 1).

In step 305, a terrestrial parameter may be received by the system. For example, terrestrial parameters may include characteristics related to geography like latitude/longitude coordinates, altitude, a specific address, a city, a county, a state, and/or a general area. In addition or alternatively, terrestrial parameters may also include characteristics related to the climate and/or turf conditions of an area. Examples of climate characteristics may include average rainfall per annum, average temperatures, average prevailing wind conditions, etc. Examples of turf conditions may include data that indicates whether a geographical area has hard turf, firm turf, moderate turf, soft turf, or wet turf.

In one or more embodiments, one or more terrestrial parameters may be received or determined via input. For example, the mobile communication device 115 of FIG. 1 may request input from the user such as: "what is your address?" or "what is your city?" or "in which area(s) do you play golf?" In another example, the mobile communication device 115 and/or sensing device 110 may utilize a Global Positioning System (GPS) to determine the current location and/or use the gathered location information to determine other terrestrial parameters such as climate or turf condition. As another example, a user may simply be queried to input to the mobile communication device 110 a terrestrial condition, such as "hard", "firm," "moderate," "soft," or "wet."

At step 310, data corresponding to a user operating a mechanical device may be received (e.g., swing sensing device 110 may detect a golfer's swing of a golf club and measure and/or calculate swing characteristics such as swing speed, swing path, etc). More specifically, a positional sensor (e.g., sensor 220) may incorporate an accelerometer that may be able to determine positions of the sensor relative to other objects and/or a clock.

At step 315, an overall factor may be determined based on the data corresponding to the user operating the mechanical device. In one embodiment, this may occur at the swing sensing device 110. Since the swing sensing device 110 might have already received the data corresponding to the user operating the mechanical device at step 310, the determination may be performed without further interaction from the mobile communication device 115. In an alternative embodiment where the determination step 315 occurs at the mobile communication device 115, however, the swing sensing device 110 may send the required data to the mobile communication device 115.

Regardless, the overall factor may be determined, in one example, using a pre-determined equation or relationship where the received data and/or calculations/information derived therefrom are inputs to the equation and the overall factor is the output. Alternatively and/or in addition, a stored look-up table or database may be used to determine the overall factor based on the received data and/or calculations/information derived therefrom.

At step 320, a recommendation may be determined based on the overall factor and the terrestrial parameter(s). In one embodiment, this may occur at the swing sensing device 110. Alternatively, in another embodiment, this may occur at the mobile communication device 115. Where it occurs at the swing sensing device 110, if necessary, the swing sensing device 110 may request and receive information from the mobile communication device 115 needed to determine the recommendation (e.g., the terrestrial parameter(s)). Where it occurs at the mobile communication device 115, if necessary, the mobile communication device 115 may request and receive information from the swing sensing device 110 needed to determine the recommendation (e.g., the overall factor).

In one or more embodiments, the recommendation may require as inputs the overall factor and the terrestrial parameters (or representative data derived therefrom). The recommendation may be determined, in one example, using a pre-determined equation where the overall factor and/or terrestrial parameters are inputs to an equation and the recommendation is based on the determined or calculated output. Alternatively and/or in addition, a stored look-up table or database may be used to determine the recommendation.

The recommendation may be related to a model type and/or specifications of a golf club that is determined to be favored for the user as it relates to the golfer's swing characteristic and the relevant terrestrial parameter(s). For example, the recommendation may be related to a fitting characteristic for a golf club.

At step 325, information related to the determined recommendation may be transmitted to an audio/visual device for displaying and/or audibly informing a user.

In one embodiment, the recommendation information may be directly sent to a customer service representative and/or a computing device whereupon the user may purchase an apparatus or device (e.g., a golf club) corresponding to or embodying the determined recommendation without expending vast amounts of additional effort and/or time. Alternatively and/or in addition, the audio/visual device outputting the recommendation to the user may be the mobile communication device 115, and contemporaneously with outputting the recommendation, the mobile communication device may also allow for the user to purchase a product corresponding to the recommendation by pressing a displayed "purchase now" soft button (not shown).

Figure 4:
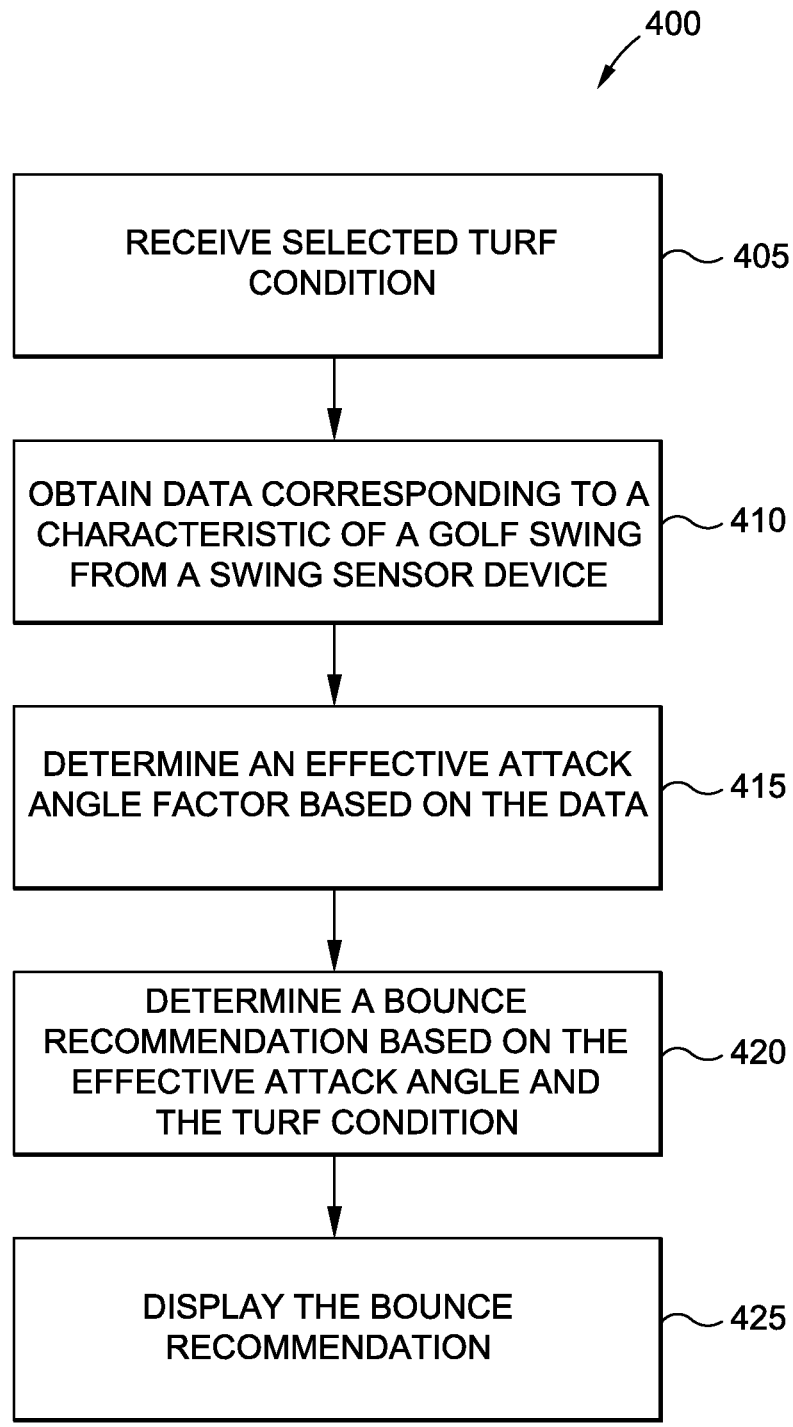
FIG. 4 illustrates a flow chart for determining a bounce recommendation based on the effective attack angle and the turf condition in accordance with one or more embodiments.
Figure 5:
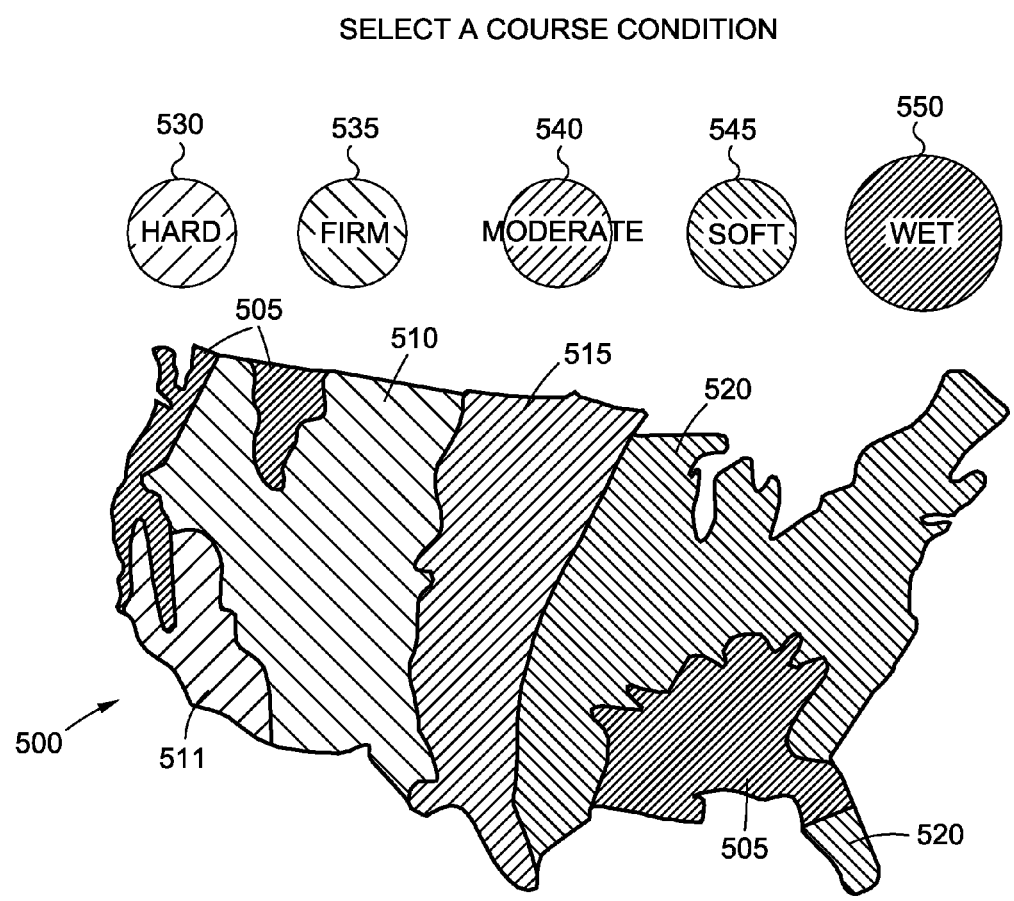
FIG. 5 is an example of a graphical user interface which allows for user selection of a terrestrial parameter in accordance with one or more embodiments.

FIG. 4 is a flow chart 400 for a recommendation engine for recommending a bounce for a wedge-type golf club. The recommendation engine may include a swing sensing device (e.g., the swing sensing device 110 of FIG. 1) and/or a computing device (e.g., a mobile communication device 115 of FIG. 1 such as a tablet computer). At step 405, a turf condition may be selected by the user or otherwise determined and received by the recommendation engine. In one embodiment, the turf conditions may be selected by the user (e.g., golfer or the club-fitting professional) and received via a touch screen interface (e.g., the display of mobile communication device 115). In one embodiment, the turf condition may be a turf firmness rating and the user may select the geographical area at which golfer prefers to play golf—upon which the system may convert the selected geographical area into a turf firmness rating. FIG. 5 illustrates an example of a graphical user interface 500 that the user might use to select the geographical area in which the golfer resides or in which the golfer desires to play golf. As shown, the map might be divided into different geographical areas. For example, the areas 505 (e.g., including portions of the west coast and portions of southeastern United States) may be predetermined to correspond to the "wet" turf designation 550. The area 510 (e.g., including portions of the mountain and desert of western United States) may correspond to a "firm" turf designation 535. The area 511 (e.g., including southwestern United States) may correspond to a "hard" turf designation 530. The area 515 (e.g., including the portions of the plains of the United States) may correspond to a "moderate" turf 540. The area 520 (e.g., including portions of midwest and the eastern seaboard of the United States) may correspond to a "soft" turf designation 545. While FIG. 5 illustrates a map of the continental United States, it will be appreciated that any map displaying relevant turf conditions for a region of interest may be used, including a world map, a map of other countries, a map of selected regions of a country or state, or even a map of a golf course of interest, given that turf conditions may vary even from hole to hole on golf courses. The user may be requested to simply touch the area of the map that corresponds to the area that the golfer prefers to play, and the computing device may convert the input to a rating of hard, firm, moderate, soft or wet depending on predetermined climate and geographical factors of the selected area.

In one or more embodiments, the selected course condition or turf condition may be given a numerical rating, for example, from 1-9 where "1" correlates to a hard turf 530, "3" correlates to a firm turf 535, "5" correlates to a moderate turf 540, "7" correlates to a soft turf 545 and a "9" correlates to a wet turf 550.

Figure 6:
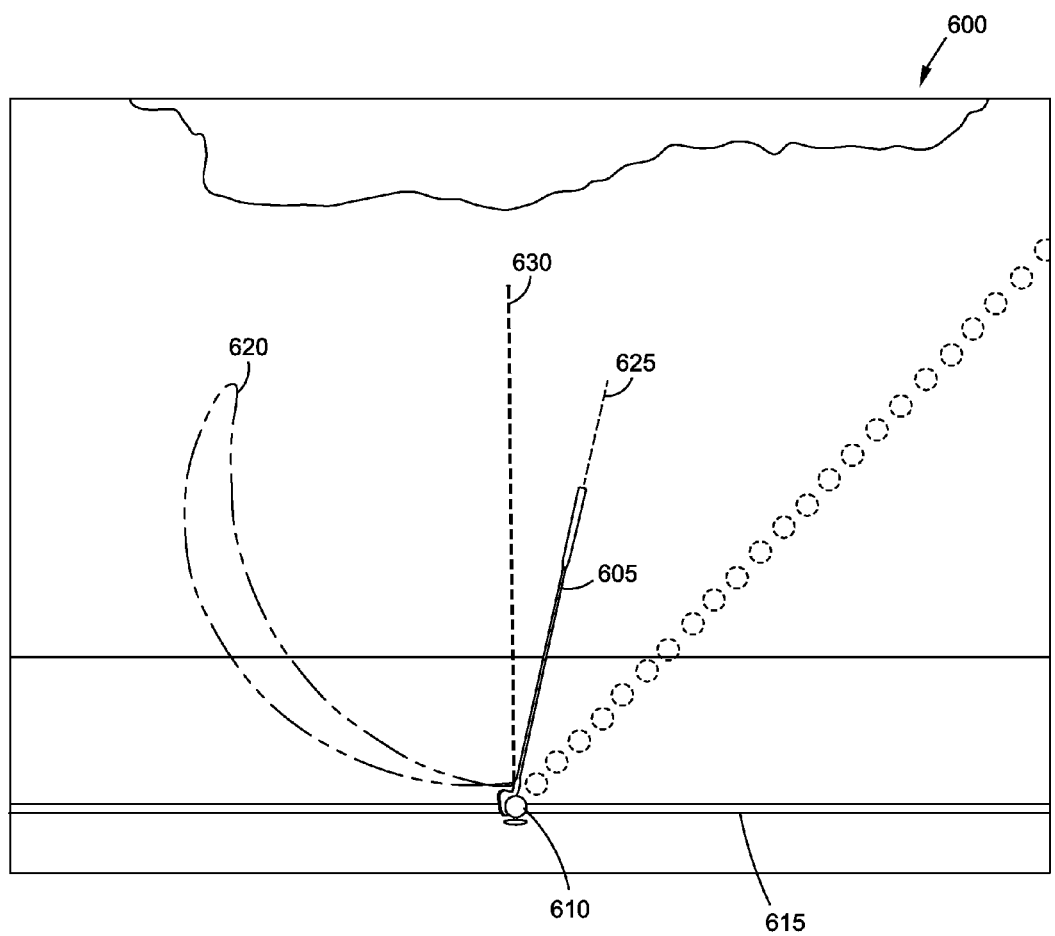
FIG. 6 is an example of a screenshot of a golfer's swing plot based on the data gathered by the swing sensor device in accordance with one or more embodiments.

Returning to FIG. 4, at step 410, the recommendation engine may obtain data corresponding to a characteristic of a golf swing from a swing sensor device. For example, the golfer may swing a golf club with a swing sensor attached thereto, and the sensor may extract, measure or otherwise calculate user-specific swing attributes, such as an attack angle and a shaft lean of the swing. In one embodiment, multiple swings may be measured and an average attack angle and/or an average shaft lean of the swing may be obtained. In a highly preferred embodiment, only three swings may be required in order to determine user-specific swing attributes. FIG. 6 is an example of a screenshot 600 of how the recommendation engine may plot a golfer's swing based on the data gathered by the swing sensor device. As shown, a virtual golf club 605 is shown in relationship to a virtual golf ball 610 and a ground plane 615. The swing path 620 taken by the club 605 may be used to determine the attack angle of the swing and the position of the shaft axis 625 at impact may be used with reference to an axis 630 normal to the ground plane 615 to determine shaft lean.

At step 415, the recommendation engine may determine an effective attack angle based on the measured attack angle and shaft lean. In one embodiment, the determination may be performed via a factor determination module (e.g, the factor determination module 280 of FIG. 2 located within, for instance, a computing device 250).

The inventors have researched swing data and have determined that these characteristics of a golf swing in combination with one another more accurately correlate to bounce, and more generally wedge-type golf club fitting. More particularly, the attack angle may be a good characteristic to base the effective attack angle on because of the strong correlation between divot and turf interaction. The shaft lean, however, also impacts the dynamic or impact bounce angle. Therefore, by using one or the other, it might not as accurate for fitting purposes as using the attack angle and shaft lean factors in combination to determine an effective attack angle.

In one embodiment, the effective attack angle may be a function of attack angle and shaft lean such that:

Effective attack angle=attack angle+(shaft lean/2).

In one embodiment, a bounce recommendation factor may replace the usage of the effective attack angle. Here, the bounce recommendation factor may be correlated with other factors including but not limited to attack angle, shaft lean, sole width, camber, sole radius or combination thereof.

Figure 7:
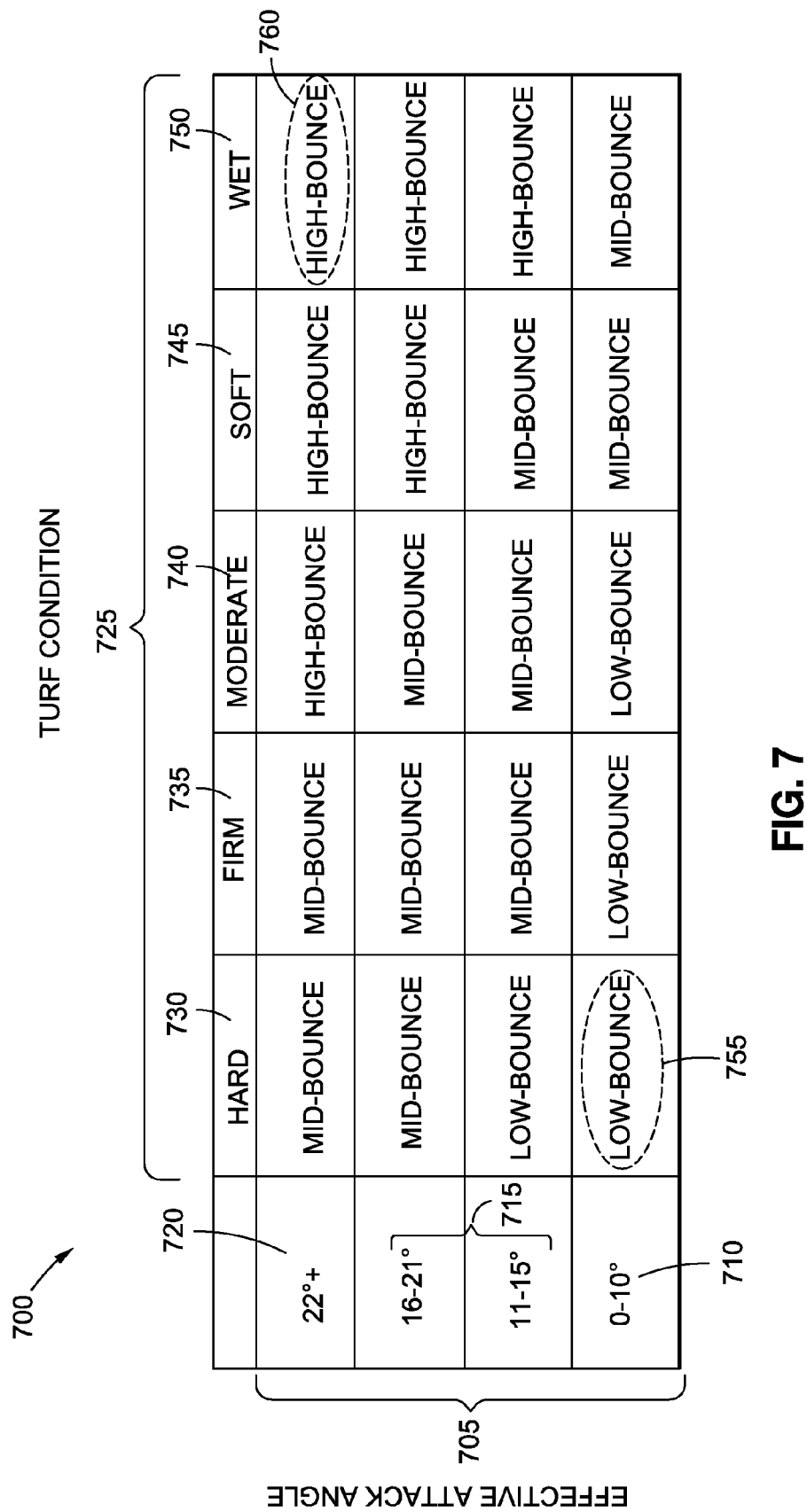
FIG. 7 illustrates a chart correlating a bounce recommendation given a particular turf condition and a particular effective attack angle in accordance with one or more embodiments.

At step 420, the recommendation engine may determine a bounce recommendation based on the effective attack angle (or, less preferably based on the attack angle alone or the shaft lean alone) and the turf condition. In one embodiment, the determination of the bounce recommendation may be performed via a selector module (e.g, the selector module 275 of FIG. 2 located within, for instance, a computing device 250). Alternatively or in addition, the recommendation engine may store in memory information defining a recommendation set correlated to effective attack angles and geographical factors. FIG. 7 illustrates an example of a recommendation set shown as chart 700 that may form the logic basis for the operation of the selector module. As shown, the full range of available effective attack angles may be subdivided into groupings 705. For example, effective attack angles of 0 to 10 degrees 710 may be approximately deemed "shallow," effective attack angles of 11 to 21 degrees 715 may be approximately deemed "moderate" and effective attack angles of 22+ degrees 720 may be approximately deemed "steep." The chart may also have columns headings 725 comprising five different headings (e.g., hard 730, firm 735, moderate 740, soft 745, and wet 750) corresponding to the different types of turf conditions available by selection by the user (e.g., via the interface 500 of FIG. 5). The four effective attack angle groupings and the five turf conditions may yield 20 intersecting possibilities, which are the bounce recommendation possibilities. For example, a shallow attack angle and a hard turf condition may correspond to a bounce recommendation of "low-bounce" (as shown in dotted circle 755), and conversely a steep attack angle of 22+ degrees and a wet turf condition may corresponding to a "high-bounce" recommendation (as shown in dotted circle 760).

Referring back to FIG. 4, at step 425, the recommendation engine may display the bounce recommendation via a display (e.g., the display of the computing unit 250). FIG. 8 illustrates an example of a bounce recommendation graph 800 which advantageously groups the effective attack angles into certain categories and correlates the effective attack angles with certain categories of turf conditions. It may allow the golfer to understand the categorization of his swing without having to refer to specific numbers that have less meaning to the average golfer. As shown, an "X" 805 may mark one intersectional location of the effective attack angle and turf intersection which determines the bounce recommendation. In this particular example, the recommendation engine may recommend a "high-bounce" (e.g., three dot) wedge because the golfer might have a "moderate" effective attack angle and may play in a "wet" turf condition. As can be seen, the turf condition has a significant impact on the bounce recommendation. With the same effective angle, a golfer who plays on "hard" turf the recommendation engine may suggest a "low bounce" (e.g., one dot) wedge type golf club. Conversely, given a "hard" turf, the only bounce options are "low-bounce" or "mid-bounce", and given a "wet" turf, the only bounce options are "mid-bounce" or "high-bounce". In this manner, the recommendation engine may be deemed to be "smart" and utilize a modeling scheme based on swing characteristics and turf conditions in recommending a certain bounce for any particular golfer utilizing the system. As shown, in one embodiment, the graph 800 may substantially correlate with chart 700 of FIG. 7 and may comprise color-coded indicia (or other indicia, i.e., patterns, textures, etc.) that may, but need not, generally correspond to color-coded or other indicia for turf/course conditions as depicted by way of example in FIG. 5.

In one embodiment, where a professional golf club fitter is involved in the fitting process, the fitter may understand that this particular swing profile is between a mid-bounce (e.g., two dot) and high-bounce (e.g., three dot) and might further advise the golfer based on other factors, such as club-head speed (which may also be determined by the sensor 110), or relying on his experience. For example a golfer with a faster club head speed might be expected to dig into the turf to a greater extent at impact than a player with a slower club head speed, in which case a professional golf club fitter might recommend the high-bounce club for the player with the faster swing speed and the mid-bounce club for the golfer with the slower swing speed, all other factors such as effective attack angle and turf conditions being equal. In an alternative embodiment, the methods, systems, and apparatus disclosed herein may also be configured to factor in club head speed in this way for determining a recommended bounce angle (or other club parameter such as sole width, camber, sole radii, etc.), particularly where a golfer is "between clubs" as determined by the bounce (or other club parameter) recommendation.

In another embodiment, the recommendation may be given for a wedge-type golf club which either directly or indirectly specifies club characteristics such as a specific or a range of bounce angles, a specific or a range of cambers, a specific or a range of sole radii and/or a specific or a range of sole widths. For example, instead of (or in addition to) suggesting "low-bounce" wedge-type golf club, the recommendation may be for a club having a particular bounce angle, or a range of sole widths.

The examples given above with respect to a wedge-type golf club are not limiting. Other embodiments with respect to other types of golf clubs such as wood-type golf clubs, iron-type golf clubs, etc. are within the spirit and scope of the disclosure.

Unless otherwise indicated, all numbers expressing quantities should be understood to have minor manufacturing tolerances, and accordingly, as used in the specification and claims are to be understood as being modified in all instances by the term "about." Thus, unless indicated to the contrary, the numerical parameters set forth in the specification and attached claims are approximations that may vary depending upon the desired properties sought to be obtained.

At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the embodiments are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein is intended merely for clarification and does not pose a limitation on the scope of the disclosure. No language in the specification should be construed as indicating any non-claimed element essential to the practice of any embodiments discussed herein.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Specific embodiments disclosed herein may be further limited in the claims using "consisting of" and/or "consisting essentially" of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments so claimed are inherently or expressly described and enabled herein.

In closing, certain embodiments are described herein, including the best mode known to the inventors. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this application includes all modifications and equivalents of the subject matter recited in the claims appended hereto as permitted by applicable law. Moreover, any combination of the above-described elements in all possible variations thereof has been contemplated by the inventors and within the scope of the disclosure unless otherwise indicated herein or otherwise clearly contradicted by context. That is, it is to be understood that the embodiments disclosed herein are illustrative of the principles of the invention, and therefore, alternative configurations may be utilized in accordance with the teachings herein. Accordingly, the present invention is not limited to that precisely as shown and described.

We claim:

1. A non-transitory computer readable storage medium storing instructions that when executed by a processor performs the steps of: receiving input corresponding to a terrestrial parameter comprising a turf condition of a geographical area; receiving data characteristic of a user operating a golf club, wherein the data characteristic of the user comprises an attack angle of the user swinging the golf club and obtained via a swing sensing device associated with the user or the golf club; determining, via a selector module, a recommended golf club specific to the user, wherein determining the recommended golf club specific to the user includes identifying a bounce recommendation based on the attack angle of the user and the turf condition of the geographical area, the recommended golf club selected from at least two possible golf clubs having different bounces; and transmitting information indicative of the recommended golf club.

2. The non-transitory computer-readable storage medium of claim 1, wherein the data representing a turf condition of the geographical area is a selected one of: hard, firm, moderate, soft, and wet.

3. The non-transitory computer readable storage medium of claim 1, wherein the golf club is a wedge-type golf club.

4. The non-transitory computer readable storage medium of claim 1, wherein the data characteristic of the user further includes a shaft lean of the user swinging a golf club at a point of impact.

5. The non-transitory computer readable storage medium of claim 4, wherein the data characteristic of the user comprises an overall factor based on an effective attack angle computed from the attack angle and the shaft lean.

6. The non-transitory computer readable storage medium of claim 5, wherein determining the recommended golf club specific to the user includes identifying a bounce recommendation based on the effective attack angle and the turf condition of the geographical area.

7. The non-transitory computer readable storage medium of claim 5, wherein the effective attack angle=attack angle+(shaft lean/2).

8. A method for obtaining a bounce recommendation, the method comprising: receiving a user-selected geographical factor; receiving characteristic data via a swing sensing device, the characteristic data corresponding to a golf swing of a user swinging a golf club; determining, using a factor determination module, an overall bounce factor based on the characteristic data; selecting, using a selector module, a bounce recommendation based on the overall bounce factor and the geographical factor; and displaying, on a graphical user interface, the selected bounce recommendation.

9. The method of claim 8, further comprising correlating the user-selected geographic factor with a turf condition.

10. The method of claim 8, wherein the characteristic data includes a shaft lean and an attack angle.

11. The method of claim 10, wherein the overall bounce factor equals attack angle+(shaft lean/2).

12. The method of claim 11, wherein selecting the bounce recommendation further includes selecting one of: high bounce, mid bounce, and low bounce based upon the overall bounce factor and the selected geographical factor.

13. The method of claim 12 wherein the method further includes determining a swing speed, and selecting a higher bounce angle for a higher swing speed and selecting a lower bounce angle for a lower swing speed.

14. A system comprising: a swing sensing device configured to obtain data corresponding to a characteristic of a golf swing, the swing sensing device further including: a sensor configured to obtain the data corresponding to the characteristic of the golf swing, and a transceiver configured to transmit the obtained data corresponding to the characteristic of the golf swing; and a display device configured to determine and display a bounce recommendation based at least in part on the data corresponding to the characteristic of the golf swing, the display device further including: an input device configured to obtain a selected geographical factor; a transceiver configured to receive the obtained data corresponding to the characteristic of the golf swing from the swing sensing device, a factor determination module configured to determine an effective attack angle based on the data received from the sensor, a memory device configured to store information defining a recommendation set, the recommendation set correlated to effective attack angles and geographical factors, a selector configured to determine a bounce recommendation from the recommendation set based on the determined effective attack angle and the user selected geographical factor, and a display configured to display the bounce recommendation.

15. The system of claim 14, wherein the sensor is attachable to a golf club shaft and wherein the display device is a mobile communication device.

16. The system of claim 14, wherein the user-selected geographical factor is correlated with a turf condition.

17. The system of claim 14, wherein data received from the sensor includes an attack angle and a shaft lean of the golf swing, and wherein the effective attack angle is calculated as attack angle+(shaft lean/2).

18. The system of claim 14, wherein determining a bounce recommendation further includes determining a bounce correlating to the user selected geographical factor and the effective attack angle.

19. The system of claim 14, wherein the bounce is one of: high bounce, mid bounce and low bounce.

20. The system of claim 19, wherein the data received from the sensor further includes swing speed, and the bounce recommendation is based at least in part on the swing speed.

* * * * *